(12) United States Patent
Koshida

(10) Patent No.: US 6,498,243 B1
(45) Date of Patent: Dec. 24, 2002

(54) EPIMORPHIN ANTAGONIST AND PROCESS FOR PRODUCING IT

(75) Inventor: Shogo Koshida, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/337,501

(22) Filed: Jun. 22, 1999

Related U.S. Application Data

(62) Division of application No. 08/981,012, filed as application No. PCT/JP97/01414 on Apr. 24, 1997, now Pat. No. 5,998,579.

(30) Foreign Application Priority Data

Apr. 24, 1996 (JP) ............................................... 8-102553
Jan. 23, 1997 (JP) ............................................... 9-010148

(51) Int. Cl.[7] .......................... C07H 21/04; C07K 7/04; C07K 14/475
(52) U.S. Cl. ..................... 536/23.5; 536/23.1; 530/300; 530/324; 530/325; 530/326
(58) Field of Search ............................. 536/23.1, 23.5; 530/300, 326, 324, 325

(56) References Cited

FOREIGN PATENT DOCUMENTS

| EP | 0562123 A1 | 9/1993 |
| EP | 0698666 A2 | 2/1996 |

OTHER PUBLICATIONS

Lodish et al. Molecular Cell Biology, 3rd edition, Mar. 1995, W. H. Freeman & Co., p. G4.*

Shi. et al., "A Recombinant Epimorphin Fragment Stimulates Wound Healing in a Normal Rabbit Ear Model", The Journal of Investigative Dermatology, Apr. 1995, vol. 104, No. 4, p. 742.

Epimorphin: A Mesenchymal Protein Essential for Epithelial Morphogenesis, Yohei Hirai et aa., Cell, vol. 69, 471–481, May 1, 1992.

* cited by examiner

Primary Examiner—David S. Romeo
(74) Attorney, Agent, or Firm—McDermott, Will & Emery

(57) ABSTRACT

This invention provides an epimorphin antagonist comprising part of the functional domain of epimorphin (e.g., a polypeptide specified by the amino acid sequence:

H-Ser(Asn)-Gly-Asn-Arg-Thr-Ser-Val-Asp-Leu-Arg-Ile-Arg-Arg-Thr-Gln-His-Ser-Val-Leu-OH SEQ ID NO: 2 and SEQ ID NO: 3) and having the activity of substantially inhibiting the morphogenic activity of epimorphins on epithelial cells, and provides a pharmaceutical containing the epimorphin antagonist as the active ingredient.

3 Claims, 8 Drawing Sheets

SEQUENCE LISTING

<160> NUMBER OF SEQ ID NOS: 10

<210> SEQ ID NO 1
<211> LENGTH: 249
<212> TYPE: DNA
<213> ORGANISM: Homo sapiens

<400> SEQUENCE: 1

```
agtgggaacc ggacttcagt ggatcttcgg atacgaagaa cccagcattc ggtgctgtct      60
cggaagtttg tggaagccat ggcggagtac aatgaggcac agactctgtt tcgggagcgg     120
agcaaaggcc gcatccagcg ccagctggag ataactggga gaaccaccac agacgacgag     180
ctagaagaga tgctggagag cgggaagcca tccatcttca cttccgacat tatatcagat     240
tcacaaatt                                                              249
```

<210> SEQ ID NO 2
<211> LENGTH: 19
<212> TYPE: PRT
<213> ORGANISM: Homo sapiens

<400> SEQUENCE: 2

```
Ser Gly Asn Arg Thr Ser Val Asp Leu Arg Ile Arg Arg Thr Gln His
 1               5                  10                  15

Ser Val Leu
```

<210> SEQ ID NO 3
<211> LENGTH: 19
<212> TYPE: PRT
<213> ORGANISM: Mus musculus

<400> SEQUENCE: 3

Asn Gly Asn Arg Thr Ser Val Asp Leu Arg Ile Arg Arg Thr Gln His
 1               5                  10                  15

Ser Val Leu

<210> SEQ ID NO 4
<211> LENGTH: 83
<212> TYPE: PRT
<213> ORGANISM: Homo sapiens

<400> SEQUENCE: 4

Ser Gly Asn Arg Thr Ser Val Asp Leu Arg Ile Arg Arg Thr Gln His
 1               5                  10                  15

Ser Val Leu Ser Arg Lys Phe Val Glu Ala Met Ala Glu Tyr Asn Glu
            20                  25                  30

Ala Gln Thr Leu Phe Arg Glu Arg Ser Lys Gly Arg Ile Gln Arg Gln
        35                  40                  45

Leu Glu Ile Thr Gly Arg Thr Thr Asp Asp Glu Leu Glu Glu Met
    50                  55                  60

Leu Glu Ser Gly Lys Pro Ser Ile Phe Thr Ser Asp Ile Ile Ser Asp
 65                  70                  75                  80

Ser Gln Ile

<210> SEQ ID NO 5
<211> LENGTH: 83
<212> TYPE: PRT
<213> ORGANISM: Mus musculus

<400> SEQUENCE: 5

Asn Gly Asn Arg Thr Ser Val Asp Leu Arg Ile Arg Arg Thr Gln His
 1               5                  10                  15

Ser Val Leu Ser Arg Lys Phe Val Asp Val Met Ala Glu Tyr Asn Glu
            20                  25                  30

Ala Gln Ile Leu Phe Arg Glu Arg Ser Lys Gly Arg Ile Gln Arg Gln
        35                  40                  45

Leu Glu Ile Thr Gly Arg Thr Thr Asp Asp Glu Leu Glu Glu Met
    50                  55                  60

Leu Glu Ser Gly Lys Pro Ser Ile Phe Ile Ser Asp Ile Ile Ser Asp
 65                  70                  75                  80

Ser Gln Ile

<210> SEQ ID NO 6
<211> LENGTH: 252
<212> TYPE: DNA
<213> ORGANISM: Homo sapiens

<400> SEQUENCE: 6
agtgggaacc ggacttcagt ggatcttcgg atacgaagaa cccagcattc ggtgctgtct      60
cggaagtttg tggaagccat ggcggagtac aatgaggcac agactctgtt tcggagcgg     120 agcaaaggcc gcatccagcg ccagctggag ataactggga gaaccaccac agacgacgag    180
ctagaagaga tgctggagag cgggaagcca tccatcttca cttccgacat tatatcagat    240

-continued

```
tcacaaatta ct                                                            252

<210> SEQ ID NO 7
<211> LENGTH: 252
<212> TYPE: DNA
<213> ORGANISM: Mus musculus

<400> SEQUENCE: 7
aatgggaacc gaacttcagt ggatctgcgg atacgaagga cccagcactc ggtgctgtca         60
cggaagtttg tggacgtcat gacagaatac aatgaagcgc agatcctgtt ccgggagcga       120
agcaaaggcc gcatccagcg ccagctggag atcactggga ggaccaccac tgacgacgag       180
ctggaagaga tgctggagag cgggaagccg tccatcttca tctcggatat tatatcagat       240
tcacaaatca ct                                                            252

<210> SEQ ID NO 8
<211> LENGTH: 84
<212> TYPE: PRT
<213> ORGANISM: Mus musculus

<400> SEQUENCE: 8
```

Asn Gly Asn Arg Thr Ser Val Asp Leu Arg Ile Arg Arg Thr Gln His
 1               5                  10                  15

Ser Val Leu Ser Arg Lys Phe Val Asp Val Met Ala Glu Tyr Asn Glu
             20                  25                  30

Ala Gln Ile Leu Phe Arg Glu Arg Ser Lys Gly Arg Ile Gln Arg Gln
         35                  40                  45

Leu Glu Ile Thr Gly Arg Thr Thr Thr Asp Asp Glu Leu Glu Glu Met
     50                  55                  60

Leu Glu Ser Gly Lys Pro Ser Ile Phe Ile Ser Asp Ile Ile Ser Asp
 65                  70                  75                  80

Ser Gln Ile Thr

```
<210> SEQ ID NO 9
<211> LENGTH: 65
<212> TYPE: PRT
<213> ORGANISM: Homo sapiens

<400> SEQUENCE: 9
```

Ser Arg Lys Phe Val Glu Ala Met Ala Glu Tyr Asn Glu Ala Gln Thr
 1               5                  10                  15

Leu Phe Arg Glu Arg Ser Lys Gly Arg Ile Gln Arg Gln Leu Glu Ile
             20                  25                  30

Thr Gly Arg Thr Thr Thr Asp Glu Leu Glu Glu Met Leu Glu Ser
         35                  40                  45

Gly Lys Pro Ser Ile Phe Thr Ser Asp Ile Ile Ser Asp Ser Gln Ile
     50                  55                  60

Thr
 65

```
<210> SEQ ID NO 10
<211> LENGTH: 65
<212> TYPE: PRT
<213> ORGANISM: Mus musculus

<400> SEQUENCE: 10
```

Ser Arg Lys Phe Val Asp Val Met Thr Glu Tyr Asn Glu Ala Gln Ile
 1               5                  10                  15

-continued

```
Leu Phe Arg Glu Arg Ser Lys Gly Arg Ile Gln Arg Gln Leu Glu Ile
            20                  25                  30

Thr Gly Arg Thr Thr Thr Asp Asp Glu Leu Glu Glu Met Leu Glu Ser
            35                  40                  45

Gly Lys Pro Ser Ile Phe Ile Ser Asp Ile Ile Ser Asp Ser Gln Ile
        50                  55                  60

Thr
65
```

EPIMORPHIN ANTAGONIST AND PROCESS FOR PRODUCING IT

This is a division of application Ser. No. 08/981,012, filed Feb. 11, 1998, now U.S. Pat. No. 5,998,579 which is a 371 of PCT/JP97/01414 filed Apr. 24, 1997.

TECHNICAL FIELD

This invention relates to polypeptides which have the activity of specifically inhibiting epimorphins (hereinafter referred to as epimorphin antagonist activity), substances promoting the morphogenesis of epithelial tissue, and which are useful as the active ingredient of pharmaceuticals.

BACKGROUND ART

The normal morphogenesis of epithelial tissue has been suggested to be controlled by factors derived from mesenchymal cells present around the epithelial tissue. Diseases ascribed to the abnormal morphogenesis of epithelial tissue are largely due to abnormalities in mesenchymal cells. These findings have aroused an interest in the clarification of the mechanism by which mesenchymal cells control the morphogenesis of epithelial tissue. However, substances involved in the control of morphogenesis of epithelial tissue are expressed under time and spatial control in a complicated system. It is extremely difficult to isolate these substances and analyze their functions. It is also difficult to construct a model experimental system simplifying the morphogenesis of epithelial tissue. For these and other reasons, much progress has not been made to date in researches in this field. Thus, analysis of the control mechanism for the morphogenesis of epithelial tissue has been demanded keenly in order to elucidate the mechanism of occurrence of diseases associated with the morphogenesis of epithelial tissue and establish methods for treating these diseases.

Under these circumstances, a report was made of success in the isolation of epimorphin taking part in the control of the morphogenesis of epithelial tissue (Japanese Laid-Open Patent Publication No. 25295/94 or European Patent Application Laid-Open Publication No. 562123, hereinafter called EPA562123). This substance was shown to be a physiologically active substance containing a protein of 277 to 289 amino acids as the core protein, and to be biosynthesized mainly by mesenchymal cells. Epimorphin was also shown to have the action of promoting the morphogenesis of epithelial tissue, and it was also indicated that when epimorphin did not function, normal tissue formation did not take place.

As a substance known to inhibit the physiological action of epimorphin (epithelial tissue morphogenesis promoting action), there is an antibody (M-1) which binds specifically to epimorphin, inhibiting its action (Japanese Laid-Open Patent Publication No. 25295/94 or EPA562123; CELL, 69, pp. 471–481, 1992). This antibody is useful for clarifying the mechanism for the normal morphogenesis of epithelial tissue by epimorphin, and is expected to be useful in the elucidation of the mechanism of occurrence of diseases ascribed to the abnormal expression (excessive expression) of epimorphin and in the prevention and treatment of these diseases. Epimorphin also acts to promote the morphogenesis of a hair follicle. Thus, the above-mentioned antibody that inhibits the activity of epimorphin is likely to induce alopecia or inhibit hair growth.

However, this antibody posed the problem of being unstable and becoming easily deactivated during preparation, thus making it difficult to develop or stably supply it as a pharmaceutical or a hair growth inhibitor. Since its molecular weight is large (more than 150,000 Kd), moreover, it was unable to pass through the keratin of the skin easily and was not expected to inhibit hair growth sufficiently. For these reasons, it has been demanded to develop a substance which inhibits the aforementioned activity of epimorphin, and which is stable and has a low molecular weight of, say, less than several thousands permitting its passage through the skin. In particular, epimorphin antagonist, a substance binding to the receptor on an epithelial cell where epimorphin binds, and being capable of inhibiting the epithelial tissue morphogenic activity of epimorphin, is expected to take marked effect in serving as the active ingredient of a pharmaceutical or a hair growth inhibitor, and in elucidating the mechanism of action of epimorphin.

In addition, in removing hair on the arm or leg, it has been customary practice to directly pull it out by means of a tape or forceps, or to apply to the site a solution containing an ingredient such as an alkali for lysis of the hair. The former method causes pain, while the latter method damages the skin. If it is possible to provide a substance acting to inhibit the function of epimorphin and having a molecular weight low enough for percutaneous absorption, therefore, such a substance is expected to be useful as the active ingredient of a hair growth inhibitor that avoids the above problems. That is, hair growth can be suppressed for a long term by applying a substance with such characteristics after shaving. This substance is usable as a hair growth inhibitor which overcomes the drawbacks of a conventional hair remover.

DISCLOSURE OF THE INVENTION

An object of the present invention is to provide a substance for inhibiting the action of epimorphin. More particularly, the invention aims to provide a substance useful as an epimorphin antagonist which specifically inhibits the morphogenic activity of epimorphin on epithelial tissue. Further, the invention aims at providing an epimorphin antagonist having such a characteristic effect, a low molecular weight, and stability.

Another object of the invention is to provide a pharmaceutical which contains as the active ingredient an epimorphin antagonist inhibiting the morphogenic activity of epimorphin on epithelial tissue, and which is useful for the prophylaxis and/or treatment of diseases attributable to the excessive expression of epimorphin.

Still another object of the invention is to provide a hair growth inhibitor which contains as the active ingredient the above-described epimorphin antagonist.

BEST MODE FOR CARRYING OUT THE INVENTION

Figure 1:
FIG. 1 is a photomicrograph of the histological shape of a mouse pulmonary primordium at the start of culture when its organ culture was performed in the presence of the epimorphin antagonist of the present invention.

To attain the aforementioned objects, the inventors have conducted extensive studies, finding that a partial sequence polypeptide contained in the functional domain of epimorphin has the activity of markedly inhibiting the morphogenic activity of epimorphin on epithelial cells and functions as an epimorphin antagonist. The present invention has been accomplished based on these findings.

In more detail, the invention provides an epimorphin antagonist having epimorphin antagonist activity and being a polypeptide comprising the following amino acid sequence:

H-X1-Gly-Asn-Arg-Thr-Ser-Val-Asp-Leu-Arg-Ile-Arg-Arg-Thr-Gln-His-Ser-Val-Leu-OH where X1 represents Ser or Asn. (SEQ ID NO: 2 and SEQ ID NO: 3)

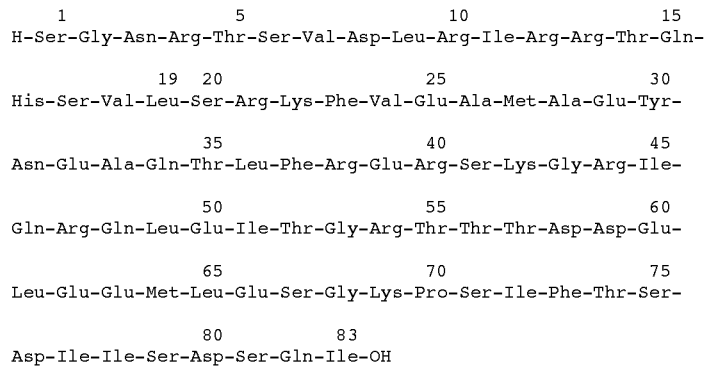

The invention also provides an epimorphin antagonist having epimorphin antagonist activity and being a polypeptide having the following amino acid sequence ranging from the 1st amino acid to the nth amino acid (n denotes an integer of 20 to 83):

H-Asn-Cly-Asn-Arg-Thr-Ser-Val-Asp-Leu-Arg-Ile-Arg-Arg-Thr-Gln-His-Ser-Val-Leu-Ser-Arg-Lys-Phe-Val-Asp-Val-Met-Thr-Glu-Tyr-Asn-Glu-Ala-Gln-Ile-Leu-Phe-Arg,-Glu-Arg-Ser-Lys-Gly-Arg-Ile-Gln-Arg-Gln-Leu-Glu-Ile-Thr-Gly-Arg-Thr-Thr-Thr-Asp-Asp-Glu-Leu-Glu-Glu-Met-Leu-Glu-Ser-Gly-Lys-Pro-Ser-Ile-Phe-Ile-Ser-Asp-Ile-Ile-Ser-Asp-Ser-Gln-Ile-OH (SEQ ID NO:5).

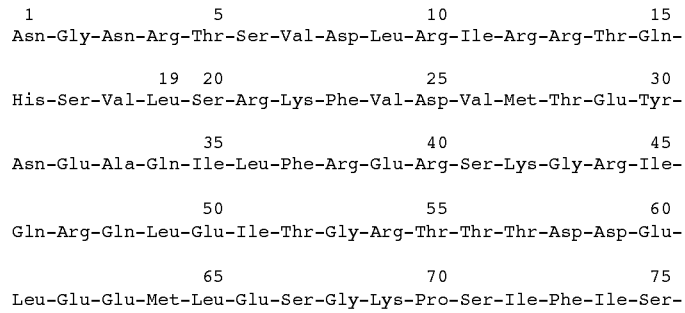

-continued

```
                     80            83
        Asp-Ile-Ile-Ser-Asp-Ser-Gln-Ile
```

The invention also provides an epimorphin antagonist comprising the above-described amino acid sequence from which, in which or to which one to several amino acids have been deleted, replaced or added, and also having epimorphin antagonist activity.

The invention also provides an epimorphin antagonist which comprises a polypeptide containing the above-described amino acid sequence as a partial sequence thereof, and which substantially has epimorphin antagonist activity.

The invention also provides an epimorphin antagonist comprising the above-described amino acid sequence in which one to several amino acids have been modified with sugars or lipids, and also having epimorphin antagonist activity.

The invention also provides an epimorphin antagonist comprising the above-described amino acid sequence in which one to several amino acids have been phosphorylated, and also having epimorphin antagonist activity.

The invention also provides an epimorphin antagonist whose epimorphin antagonist activity inhibits the morphogenic activity of epimorphins on epithelial tissue.

The invention also provides an epimorphin antagonist whose epimorphin antagonist activity inhibits the morphogenic activity of epimorphins on a hair follicle.

The invention also provides a pharmaceutical composition containing the above-described epimorphin antagonist as the active ingredient.

The invention also provides the above-described pharmaceutical composition for use in the treatment and/or prevention of disease ascribed to the excessive expression of epimorphin.

The invention also provides the above-described pharmaceutical composition in which the disease ascribed to the excessive expression of epimorphin is hyperepimorphinism.

The invention also provides the above-described pharmaceutical composition which is used as a hair growth inhibitor.

The invention also provides a polynucleotide encoding the aforementioned polypeptide.

The above-described polypeptides provided by the invention have the activity of inhibiting the morphogenic activity of epimorphins on epithelial cells. Thus, the present invention provides epimorphin antagonists comprising the polypeptides. The term "epimorphins" in the present specification is used to express a concept including naturally occurring epimorphin, a modified form of the natural type epimorphin that has substantially the same physiological activity as the natural epimorphin (i.e. modified epimorphin), and amino acid variants of the natural type epimorphin and the modified epimorphin that have substantially the same physiological activity as the natural epimorphin. The epimorphin antagonist of the present invention has the activity of inhibiting the morphogenic activity of any substances selected from the group consisting of the natural type epimorphin, the modified epimorphin, and their amino acid variants.

In the present specification, the natural type epimorphin refers to epimorphin biosynthesized by mesenchymal cells of, say, mammals. Examples of the natural type epimorphin include epimorphin derived from animals such as human, monkey, cattle, horse, sheep, dog, cat, rabbit, rat and mouse, preferably, human-derived epimorphin. Among the natural type epimorphin may be a plurality of isoforms produced by genetic splicing. Among the human epimorphins, for instance, there are human epimorphin consisting of 288 amino acids, and isoforms A and B of human epimorphin composed of 287 and 277 amino acids, respectively, as described in Japanese Laid-Open Patent Publication No. 25295/94. The mouse epimorphin includes mouse epimorphin consisting of 289 amino acids, and isoforms A and B of mouse epimorphin composed of 288 and 279 amino acids, respectively. The term "natural type epimorphin" in the present specification is used to express a concept including all of these isoforms.

In the present specification, the modified epimorphin refers to a polypeptide which has substantially the same physiological activity as the natural type epimorphin (e.g., cell adhesion to epithelial cells and morphogenesis promotion for epithelial cells) and which either is a partial polypeptide sequence derived from the polypeptide sequence of the natural type epimorphin (normally a polypeptide comprising 277 to 289 amino acids), or contains as its partial sequence the partial polypeptide sequence derived from the polypeptide sequence of the natural type epimorphin. The natural type epimorphin has a coiled coil area (1) on the N-terminal side, a functional domain (2) in the middle, a coiled coil area (3) on the C-terminal side, and a hydrophobic area at the C-terminal, and binds to the cell membrane at the C-terminal hydrophobic area. A method for removing the C-terminal hydrophobic area has been proposed with a view to solubilizing the natural type epimorphin (Japanese Laid-Open Patent Publication No. 25295/94). A polypeptide produced by such a method is a typical compound falling in the category of the modified epimorphin.

In the present specification, the amino acid variant of the natural type epimorphin or the modified epimorphin refers to a polypeptide which has substantially the same physiological activity as the natural type epimorphin and in which one or more of the amino acids constituting the polypeptide chain of the natural type epimorphin or the modified epimorphin have been replaced by other amino acids, or in which one or more of these constituent amino acids have been deleted, and/or in which one or more arbitrary amino acids have been inserted into this polypeptide chain.

More concretely, the natural type epimorphin is disclosed, for example, in Japanese Laid-Open Patent Publication No. 25295/94 as human- or mouse-derived epimorphin and isoforms thereof. Typical examples of the modified epimorphin are, in addition to the above-mentioned modified epimorphin (Japanese Laid-Open Patent Publication No. 25295/94 or EPA562123), modified epimorphin produced by adding a hydrophilic polypeptide comprising 5 to 99 amino acids to at least one end of a polypeptide containing the functional domain of epimorphin (Japanese Laid-Open Patent Publication No. 325293/96 or European Patent Application Laid-Open Publication No. 698666 (hereinafter called EPA698666)), and modified epimorphin comprising a polypeptide of the structure in which the hydrophobic area at the C-terminal has been deleted from the entire length of the epimorphin having the coiled coil area (1) on the N-terminal side, functional domain (2) in the middle, coiled coil area (3) on the C-terminal side, and hydrophobic area at the C-terminal, and in which at least some amino acids have been deleted from at least one terminal side of the coiled coil areas (1) and (3) (Japanese Laid-Open Patent Publication No. 65885/97 or EPA698666).

It should be understood that besides all the modified epimorphins disclosed in the above-quoted publications and specifications, modified epimorphins producible by the methods disclosed in these publications and specifications, or changed or modified forms of these methods, are all included in the modified epimorphin in the present specification as long as they fulfill the aforementioned definitions. Methods for producing the amino acid variant of the natural type epimorphin or the modified epimorphin are explained concretely, for example, in Japanese Laid-Open Patent Publication No. 325293/96 and Japanese Laid-Open Patent Publication No. 65885/97 or EPA698666. However, they are not restricted to these methods, and amino acid variants produced by any methods are available. The testing of the physiological activity of these modified epimorphins or their amino acid variants can be performed in accordance with the testing method for the physiological activity of the natural type epimorphin that has been described in detail in Japanese Laid-Open Patent Publication No. 25295/94 or EPA562123. Concretely, it suffices to confirm the morphogenic activity like branching morphogenesis of a mouse fetal lung or a mouse fetal skin morphogenesis that is described in the Examples of the present specification.

The epimorphin antagonist of the present invention has the feature of inhibiting the morphogenic activity of the above-described epimorphins on epithelial cells (hereinafter, this feature may be referred to herein as "epimorphin antagonist activity"). As the epimorphin antagonist of the present invention, there is provided an epimorphin antagonist which comprises part of the functional domain of epimorphin and substantially has the epimorphin antagonist activity. As an embodiment thereof, polypeptide (I) is provided which is specified by the following amino acid sequence:

H-Ser(Asn)-Gly-Asn-Arg-Thr-Ser-Val-Asp-Leu-Arg-Ile-Arg-Arg-Thr-Gln-His-Ser-Val-Leu-OH (where the amino acid residue at the N-terminal maybe replaced by the parenthesized amino acid residue, each amino acid residue preferably represents an L-amino acid residue; this sequence is designated as H-S(N)GNRTSVDLRIRRTQHSVL-OH according to one-letter designation) (SEQ ID NO: 2 and SEQ ID NO: 3).

The polypeptide (I) is a partial sequence of the functional domain of epimorphin (an amino acid sequence ranging from the 104th to 187th amino acids counting from the N-terminal in the case of natural type human epimorphin, an amino acid sequence ranging from the 105th to 188th amino acids counting from the N-terminal in the case of natural type mouse epimorphin; see Japanese Laid-Open Patent Publication No. 325293/96 or EPA698666), and corresponds to an amino acid sequence ranging from the 1st to 19th amino acids of the functional domain. This functional domain has so far been shown to exhibit adhesion to and morphogenesis promotion for epithelial cells, but has not been reported to show epimorphin antagonist activity. Nor is there any report on the production of this polypeptide.

The epimorphin antagonist of the present invention includes not only the polypeptide (I), but also an amino acid variant of the polypeptide (I) in which one or more of its constituent amino acids have been replaced by other amino acids, or in which one or more of these constituent amino acids have been deleted, and/or in which one or more arbitrary amino acids have been inserted into the polypeptide chain thereof, and which is a polypeptide substantially having epimorphin antagonist activity. The kinds of the one or more amino acids to replace and/or to be inserted are not restricted, but they are preferably L-amino acids.

The epimorphin antagonist of the present invention includes a polypeptide which contains the polypeptide (I) or its variant as a partial sequence thereof and which substantially has epimorphin antagonist activity. For example, one or more amino acids may be bonded to the N-terminal and/or C-terminal of the polypeptide (I), and preferably, an arbitrary oligopeptide composed of two or more arbitrary amino acids may be bonded thereto. The kinds of such amino acids are not restricted, but are preferably selected from L-amino acids. For instance, a polypeptide comprising the polypeptide (I) to whose N-terminal about 1 to 10, preferably 5 to 7, more preferably 6, L-histidines have been linked as a tag sequence is preferred from the point of view of purification efficiency.

Epimorphin antagonist as another embodiment of the present invention is polypeptide (II) specified by an amino acid sequence ranging from the I st (N-terminal) to the nth (n denotes an integer of 20 to 83) amino acid in the following amino acid sequence (A):

H-Ser(Asn)-Gly-Asn-Arg-Thr-Ser-Val-Asp-Leu-Arg-Ile-Arg-Arg-Thr-Gln-His-Ser-Val-Leu-Ser-Arg-Lys-Phe-Val-Glu(Asp)-Ala(Val)-Met-Ala(Thr)-Glu-Tyr-Asn-Glu-Ala-Gln-Thr(Ile)-Leu-Phe-Arg-Glu-Arg-Ser-Lys-Gly-Arg-Ile-Gln-Arg-Gln-Leu-Glu-Ile-Thr-Gly-Arg-Thr-Thr-Thr-Asp-Asp-Glu-Leu-Glu-Glu-Met-Leu-Glu-Ser-Gly-Lys-Pro-Ser-Ile-Phe-Thr(Ile)-Ser-Asp-Ile-Ile-Ser-Asp-Ser-Gln-Ile-OH (where the amino acid residue located on the left of the parentheses ( ) may be replaced by the parenthesized amino acid residue, and each amino acid residue preferably represents an L-amino acid residue) (SEQ ID NO: 4 and SEQ ID NO: 5). This amino acid sequence corresponds to a sequence specified by the 1st to 83rd amino acids in the polypeptide sequence of the functional domain of epimorphins.

The epimorphin antagonist of the present invention includes not only the polypeptide (II) selected from the amino acid sequence (A), but also a variant of the polypeptide (II) in which one or more of its constituent amino acids have been replaced by other amino acids, or in which one or more of these constituent amino acids have been deleted, and/or in which one or more arbitrary amino acids have been inserted into the polypeptide chain thereof and, which is a polypeptide substantially having epimorphin antagonist activity. The kinds of the one or more amino acids to replace and/or to be inserted are not restricted, but they are preferably L-amino acids.

The epimorphin antagonist of the present invention also includes a polypeptide which contains the polypeptide (II) or its variant as a partial sequence thereof-and which substantially has epimorphin antagonist activity. For example, one or more amino acids: may be bonded to the N-terminal and/or C-terminal of the polypeptide, and preferably, an oligopeptide of an arbitrary length composed of two or more arbitrary amino acids may be bonded thereto. The kinds of such amino acids are not restricted, but are preferably selected from L-amino acids. For instance, a polypeptide comprising the above polypeptide to whose N-terminal about 1 to 10, preferably 5 to 7, more preferably 6, L-histidines have been linked as a tag sequence is preferred from the point of view of purification efficiency.

However, a polypeptide comprising the polypeptide (II) to whose C-terminal threonine (Thr) has been linked has been demonstrated to act as the functional domain of the natural type epimorphin. Thus, it is not preferred that one L-threonine (L-Thr) is linked to the C-terminal of the polypeptide (II). For the same reason, it is not preferred that a polypeptide specified by the sequence H-Ser-Arg-Lys-Phe-Val-Glu(Asp)-Ala(Val)-Met-Ala(Thr)-Glu-Tyr-Asn-Glu-Ala-Gln-Thr(Ile)-Leu-Phe-Arg-Glu-Arg-Ser-Lys-Gly-Arg,-Ile-Gln-Arg-Gln-Leu-Glu-Ile-Thr-Gly-Arg-Thr-Thr-Thr-Asp-Asp-Glu-Leu-Glu-Glu-Met-Leu-Glu-Ser-Gly-Lys-Pro-Ser-Ile-Phe-Thr(Ile)-Ser-Asp-Leu-Ile-Ser-Asp-Ser-Gln-Ile-Thr-OH (where the amino acid residue located on the left of the parentheses ( ) may be replaced by the parenthesized amino acid residue, and each amino acid residue preferably represents an L-amino acid residue is linked to the C-terminal of the polypeptide (I)) (SEQ ID NO: 9 and SEQ ID NO: 10).

The polypeptide of the present invention that has been described in each of the embodiments may be in free form, but may be supplied as an acid added salt such as hydrochloride, acetate or p-toluenesulfonate, or a base added salt such as ammonium salt or organic amine salt. Thus, the polypeptide in the present specification should be interpreted as including the polypeptide in the form of the salt. Furthermore, the above polypeptide having arbitrary sugars (monosaccharides, disaccharides, oligosaccharides or polysaccharides) or lipids linked thereto, and the polypeptide which has been phosphorylated, are also included in the scope of the epimorphin antagonist of the present invention.

The Examples in the present specification concretely describe the testing methods for typical examples of epimorphin antagonist activity, i.e., the activity of inhibiting the morphogenesis of the bronchus of a mouse fetal lung and the activity of inhibiting the morphogenesis of a mouse fetal maxillary skin, in regard to the polypeptide (I) as a preferred embodiment of the epimorphin antagonist of the present invention. Thus, those skilled in the art can easily make sure, by reference to these testing examples or through a suitable change or modification of these methods, that each of the polypeptides defined above has the desired epimorphin antagonist activity. The morphogenesis promoting action of epimorphin on epithelial tissue is described in detail, for instance, in the Examples of Japanese Laid-Open Patent Publication No. 25295/94 or EPA562123. The application of the testing system described there enables epimorphin antagonist activity to be confirmed.

The Examples in the present specification demonstrate the polypeptide (I), a particularly preferred embodiment of the present invention, to have cell adhesion properties similar to those of epimorphins. By referring to those testing examples or adding a suitable change or modification to those methods, it becomes possible to confirm easily that each of the polypeptides has cell adhesion properties. The inventors do not stick to any particular theory, but the epimorphin antagonist of the invention has the property of binding to an epimorphin receptor present on the extracellular surface of an epithelial cell. This antagonist shows the same cell adhesion as do epimorphins, but upon binding to the receptor, it has no morphogenesis promoting action as exhibited by epimorphins, or cannot fully show this action. Hence, the epimorphin antagonist of the invention may act as a competitive inhibitor for epimorphins.

The epimorphin antagonist activity of the epimorphin antagonist of the invention is not restricted in terms of the potency of its inhibitory activity as long as this antagonist can substantially inhibit the morphogenetic action of epimorphins on epithelial tissue. Preferably, however, the antagonist should have epimorphin antagonist activity comparable, for instance, to that of the polypeptide (I). The Examples in the present specification describe typical examples of epimorphin antagonist activity. However, the epimorphin antagonist activity is not restricted to these examples, but should be interpreted more broadly. Any action which inhibits the morphogenesis promoting action of epimorphins on epithelial cells by any mechanism is, needless to say, included in the epimorphin antagonist activity of the epimorphin antagonist of the present invention.

The epimorphin antagonist of the invention can be synthesized by a chemical technique in customary practice for peptide synthesis, such as the solid phase or liquid phase method. The protective group for an amino group or the like, and the condensation agent for a condensation reaction, in peptide synthesis include, for example, those described in Suzuki, K.: "Protein Engineering—Basis and Application" (1992, Maruzen Co., Ltd.); Pondanski et al.: "Peptide Synthesis" (1976, John Wiley & Sons, N.Y.); and Stewart et al.: "Solid Phase Peptide Synthesis" (1969, W. H. Freeman and Co., San Francisco). With the solid phase method, commercially available various peptide synthesizers can be utilized. The Examples in the present specification describe a concrete method for producing the polypeptide (I) by means of a peptide synthesizer.

An ordinary biological method such as a gene expression procedure is also available. In this case, a recombinant vector containing a DNA sequence encoding the polypeptide chain of the epimorphin antagonist of the present invention is used to prepare a microorganism transformed by the vector (transformant). The desired polypeptide, epimorphin antagonist, can be separated and purified from a culture of the transformant. Of course, the production method for the epimorphin antagonist of the invention is not restricted to the above-described methods.

DNA usable for the method of production by gene expression includes, for example, DNA specified by the 1st nucleotide to the 57th nucleotide in the following base sequence:

AGTGGGAACC GGACTTCAGT GGATCTTCGG ATACGAAGAA 40

CCCAGCATTC GGTGCTGTCT CGGAAGTTTG TGGAAGCCAT 80

GGCGGAGTAC AATGAGGCAC AGACTCTGTT TCGGGAGCGG 120
AGCAAAGGCC GCATCCAGCG CCAGCTGGAG ATAACTGGGA 160
GAACCACCAC AGACGACGAG CTAGAAGAGA TGCTGGAGAG 200
CGGGAAGCCA TCCATCTTCA CTTCCGACAT TATATCAGAT 240
TCACAAATT(249) (SEQ ID NO: 1)

or DNA specified by the 1st nucleotide to the (3×kth) nucleotide (k denotes an integer of 20 to 83) in the above-based sequence (only the sense strand is shown with complimentary base sequence being omitted). This DNA corresponds to the 1 st to 249th nucleotides of DNA comprising the base sequence designated as SEQ ID NO: 6 in the Sequence Listing that encodes a polypeptide as the functional domain of natural type human epimorphin.

Similarly, of DNA corresponding to the 1st to 249th nucleotides of DAN comprising the base sequence designated as SEQ ID NO: 7 in the Sequence Listing that encodes a polypeptide as the functional domain of natural type mouse epimorphin, there can be utilized DNA specified by the 1st nucleotide to the 57th nucleotide; or DNA specified by the 1st nucleotide to the (3×mth) nucleotide (m denotes an integer of 20 to 83).

Using these DNA's, amino acid variants can be easily produced by the customary method. Usable as this method is, for example, the recombinant PCR method described on pages 155–160 of "PCR Experimental Manual (1991, HJB Publishing Bureau), or the PCR-based method for preparation of a mutant gene described on pages 63–67 of "Experimental Medicine, Special Issue, Vol. 8, No. 9" (1990, Shodo-sha). To produce the desired polypeptide, the method for gene expression may be, but not restricted to, the method described in detail in the Examples of Japanese Laid-Open Patent Publication No. 65885/97 or EPA698666.

The epimorphin antagonist of the present invention is useful against the excessive expression of various morphogenetic factors typified by natural type epimorphin, and preferably useful as the active ingredient of a pharmaceutical for the treatment and/or prevention of diseases associated with the excessive expression of natural type epimorphin, or as the active ingredient of a pharmaceutical for the diagnosis of such diseases. The epimorphin antagonist of the present invention is also useful as the active ingredient of a pharmaceutical for the treatment of hyperepimorphinism induced by epimorphins which are administered for the treatment and/or prevention of diseases associated with the minimal expression of natural type epimorphin. Furthermore, the epimorphin antagonist of the present invention is useful as the active ingredient of a pharmaceutical for use as a hair growth inhibitor. The term "pharmaceutical" in the present specification is used in its broadest sense, including ones for use in the prevention, treatment and diagnosis of diseases in mammals including human, as well as hair growth inhibitors which are normally classified as quasi-drugs.

As morphogenetic factors, various ones including natural type epimorphin are suggested to exist. Diseases caused by the excessive expression of one or more of these factors include, for example, rheumatoid arthritis, carcinoma such as renal carcinoma or skin carcinoma, arteriosclerosis, collagen disease, hematopoietic disease, renal disease, muscular dystrophy, osteoporosis, neurofibromatosis, Sturge-Weber syndrome, tuberous sclerosis, impaired neural tube closure, segmental disorder, vagal disorder, callosal agenesis, porencephaly, and hydrocephalus. The pharmaceutical of the invention can be expected to prove useful for the treatment and/or prevention, as well as diagnosis, of these diseases. However, the objects to which the pharmaceutical of the invention is applied to are not restricted to these diseases. It should be understood that diseases which may be associated with the excessive expression of one or more morphogenetic factors, especially epimorphin, are all included in the scope of the targets for application of the pharmaceutical of the invention. The uses of a hair growth inhibitor containing epimorphin antagonist as the active ingredient, an embodiment of the pharmaceutical of the invention, should be interpreted in the broadest sense, including those for alopecia, inhibition of hair growth, and inhibition of trichogenesis.

As the pharmaceutical of the invention, one or more substances selected from among epimorphin antagonists which are the aforementioned polypeptides may be used as such. Normally, however, it is preferred that one or more pharmaceutically acceptable pharmaceutical additives be used to produce a pharmaceutical composition containing one or more of the above substances as the active ingredient, and this composition be used for the treatment and/or prophylaxis of the aforesaid diseases. From the viewpoints of solubility, pharmacokinetics such as absorption and excretion and/or the production method, those polypeptides may be in the form of pharmaceutically acceptable salts. The route of administration of the pharmaceutical composition includes, for example, systemic administration such as intravenous, rectal or oral administration, as well as local administration such as external application, ophthalmic instillation, nasal instillation, otic instillation, or local injection.

For example, drugs for systemic administration such as intravenous injections or drip infusions, or drugs for local administration such as ointments, creams, plasters or local injections are preferred forms of the pharmaceutical composition of the present invention. The use of a pharmaceutical composition containing the active ingredient encapsulated in liposome or the like, or a pharmaceutical composition having antibodies or the like bound thereto may be able to improve its affinity or selectivity for the target organ. Of course, the route of administration may be selected suitably according to the type of disease to be targeted, the purpose of treatment or prevention, the kind of the lesion, and the condition of the patient. The dosage form preferred for the route of administration may also be chosen suitably. The form of the pharmaceutical composition when used as a diagnostic reagent is not restricted, and includes its in vivo administration to the patient and its in vitro use on samples taken from the patient.

A hair growth inhibitor containing one or more substances selected from the epimorphin antagonists of the invention as the aforementioned polypeptides is preferably supplied as a preparation in the form preferred for the purpose of use as a hair growth inhibitor, such as cream, spray, coating solution, or plaster. The polypeptide may be in the form of a pharmaceutically acceptable salt. It is also preferred that a suitable surface active agent or a liposoluble material is blended with its cream in order to allow the efficient percutaneous absorption of the epimorphin antagonist, i.e., the active ingredient, through the keratin layer of the skin.

EXAMPLES

The present invention will be described further concretely by the following Examples, but the scope of the invention is not limited thereto:

Example 1

Production of Epimorphin Antagonist of the Invention

A polypeptide having an amino acid sequence of 19 amino acids ranging from the 1st (N-terminal) amino acid to the 19th amino acid in the functional domain (the amino acid sequence described as SEQ ID NO: 8 in the Sequence Listing) in the middle of natural type mouse epimorphin was chemically synthesized using a peptide synthesizer (Advanced Chemtech 396 Synthesizer). This material was purified by means of reversed phase HPLC under the following conditions to obtain polypeptide A with a purity of more than 90%.

Column: Reversed phase Perseptive Biosystems Poros R2

Adsorption buffer: 0.1% aqueous solution of trifluoroacetic acid

Elution buffer:
  Solution A (0.1% aqueous solution of trifluoroacetic acid)
  Solution B (acrylonitrile incorporating 0.1% aqueous solution of trifluoroacetic acid)
  Elution with 76.2% solution A +23.8% solution B in 2.015 minutes.

Similarly, polypeptide B having an amino acid sequence of 39 amino acids ranging from the 1st (N-terminal) amino acid to the 39th amino acid, and polypeptide C having an amino acid sequence of 41 amino acids ranging from the 1st (N-terminal) amino acid to the 41st amino acid, in the functional domain (the amino acid sequence described as SEQ ID NO: 8 in the Sequence Listing) in the middle of natural type mouse epimorphin were obtained by synthesis and purification by means of the same reversed phase HPLC. Each polypeptide had a purity of more than 90%.

Polypeptide B: Elution with 93.7% solution A+6.3% solution B in 9.27 minutes

Polypeptide C: Elution with 93.a% solution A+6.2% solution B in 9.18 minutes

Example 2

Production of Modified Epimorphin cDNA's encoding a fragment of mouse-derived epimorphin deprived of the hydrophobic area at the C-terminal, and the functional domain in the middle of the epimorphin (fragment (123) and fragment (2), respectively, described in the Example of Japanese Laid-Open Patent Publication No. 65885/97 or EPA698666) were prepared by PCR in accordance with the method described in the Example of Japanese Laid-Open Patent Publication No. 65885/97 or EPA698666. Then, they were integrated into the NdeI and NheI sites of pET3C vector having the area between two Eco RV sites deleted therefrom to construct an expression vector. Then, this expression vector was introduced into $E.$ $coli$ BL21 strain turned into competent cells by the Hanahan method ("Lab Manual Genetic Engineering", Maruzen Co., Ltd.). The introduction of the vector was performed by adding an expression vector solution (1 mg/ml solution, 1 $\mu$l) into a solution (100 $\mu$l) of the competent cells on ice, allowing the mixture to stand for 10 minutes on ice, leaving this mixture to stand in an incubator for 2 minutes at 42° C., and then allowing the system to stand for 30 minutes on ice.

Then, the $E.$ $coli$ cells were cultured on an LB plate (1% Bacto tryptone, 0.5% Bacto-yeast extract, 1% NaCl, 1.5% Bacto-agar) containing 50 $\mu$g/ml ampicillin, and colonies which were growing were selected. These transformants were examined by the PCR method for DNA encoding the desired modified epimorphin. It was confirmed that 9 of 10 strains were the desired transformants retaining the expression vector. The resulting transformants were mass cultured by 37° C. shake culture in a liquid LB culture medium (1% Bacto tryptone, 0.5% Bacto-yeast extract, 1% NaCl) containing 50 $\mu$g/ml ampicillin. Then, IPTG, a material for inducing expression, was added into the culture medium to a final concentration of 1 mM. Further, shake culture was continued for 2 hours at 37° C. to express modified epimorphins (fragment (123) and fragment (2) in the $E.$ $coli$ cells.

Analysis of the total protein in the $E.$ $coli$ cells by SDS-polyacrylamide electrophoresis showed that the desired modified epimorphins were produced in nearly equal amounts. The above-mentioned transformants that expressed the modified epimorphins were suspended and washed in a lysis buffer [50 mM Tris-HCl (pH 8.0), 1 mM EDTA, 100 mM NaCl], and centrifuged to precipitate the cells. The cells were suspended in the lysis buffer, and then a lysozyme (SIGMA, L-6876) was added to a concentration of 1 mg/ml. Freeze-thawing was repeated 3 times to lyse the $E.$ $coli$. After ultrasonication, the supernatant was removed by centrifugation. The precipitate was washed 4 times with 2M urea/lysis buffer. Then, the precipitate was resuspended in 8M urea/lysis buffer, and centrifuged to obtain a supernatant fraction (purity: more than 90%) containing the desired modified epimorphins.

Example 3

Cell Adhesion

The polypeptides A, B and C of the present invention obtained in Example 1, and the modified epimorphins (fragment (123) and fragment (2), each having the same cell adhesion capacity as that of natural type epimorphin) were coated on suspension culture medium dishes. After drying, the dishes were washed once with 8M urea/lysis buffer. Then, the dishes were washed 5 times with PBS$^-$, and the cell strain C3H/10T1/2clone8 (Dainippon Pharmaceutical Co., Ltd., 08-226) was sprinkled on the dishes using D-MEM/F-12 culture medium (GIBCO BRL, 12400-024; hereinafter called "DH medium") containing 20 mg/ml bovine serum albumin (SIGMA, A-7030). One hour later, the dishes were washed 3 times with PBS$^-$, and then the cells were collected using 0.5N NaOH. The O.D. at 260 nm was measured to determine the number of the cells bound to the dishes. The cell count was used as an indicator of the cell adhesion of each specimen. The O.D.'s found were 1.5237 for polypeptide A, 1.4251 for polypeptide B, 1.4697 for polypeptide C, 1.4959 for fragment (123), 1.4478 for fragment (2), and 0.0194 for control (untreated). Thus, polypeptides A, B and C were all confirmed to show cell adhesion comparable to that of the modified epimorphins.

Example 4

Inhibitory Action on Morphogenesis of Bronchus

Figure 2:
FIG. 2 is a photomicrograph of the histological shape after 3 days of culture when the organ culture of the mouse pulmonary primordium was performed in the presence of the epimorphin antagonist of the present invention.
Figure 3:
FIG. 3 is a photomicrograph of the histological shape of a mouse pulmonary primordium at the start of culture when its organ culture was performed in the absence of the epimorphin antagonist of the present invention.
Figure 4:
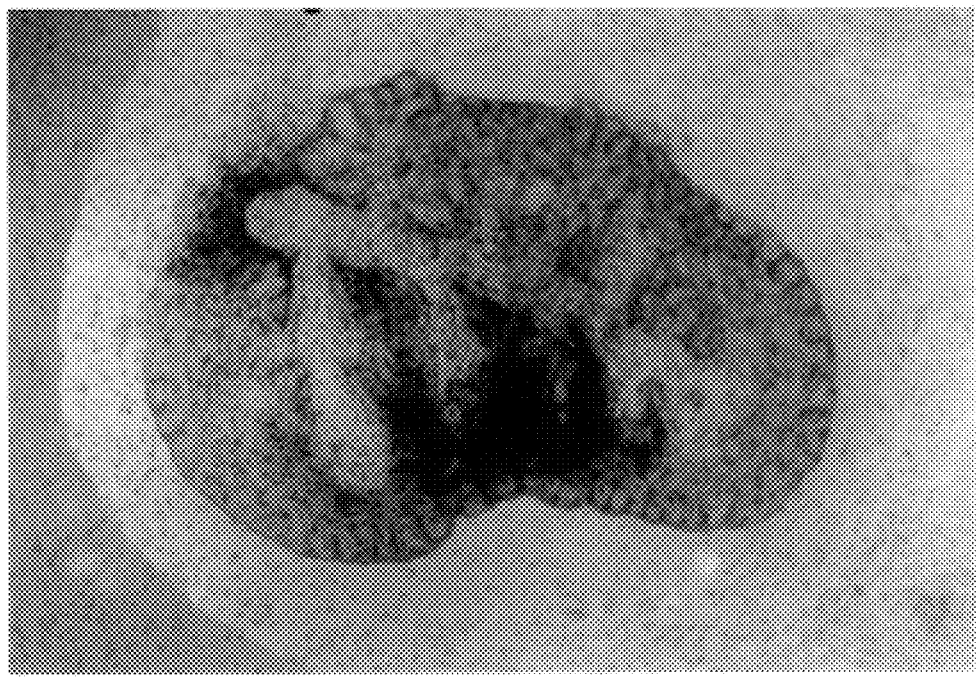
FIG. 4 is a photomicrograph of the histological shape after 3 days of culture when the organ culture of the mouse pulmonary primordium was performed in the absence of the epimorphin antagonist of the present invention.

A pulmonary primordium was removed from the fetus of the ICR pregnant mouse (Nippon Charles River, 12 days of gestation) under a stereoscopic microscope. The pulmonary primordium taken was placed on Nuclepore membrane filter (SN 110419) floated on a culture medium (DH medium, or 0.35 mg/ml polypeptide A-containing DH medium). Organ culture was performed in 5% $CO_2$ at 37° C. to investigate the effect of polypeptide A on the morphogenesis of the bronchus. As shown in FIGS. 3 and 4, when organ culture used DH medium, the morphogenesis of the bronchus normally proceeded, and finely branched bronchus formation was confirmed at completion of culture. When the pulmonary primordium was organ cultured in the culture medium containing polypeptide A, on the other hand, the morphogenesis of the bronchus was markedly inhibited (FIGS. 1 and 2). This manner of inhibition of morphogenesis was exactly the same as in treatment with MC-1, i.e., antibodies inhibiting the function of epimorphin. Hence, it is clear that the polypeptide A of the present invention inhibits the morphogenetic action of epimorphin on a pulmonary primordium.

Example 5

Inhibitory Action on Morphogenesis of Maxillary Skin

Figure 5:
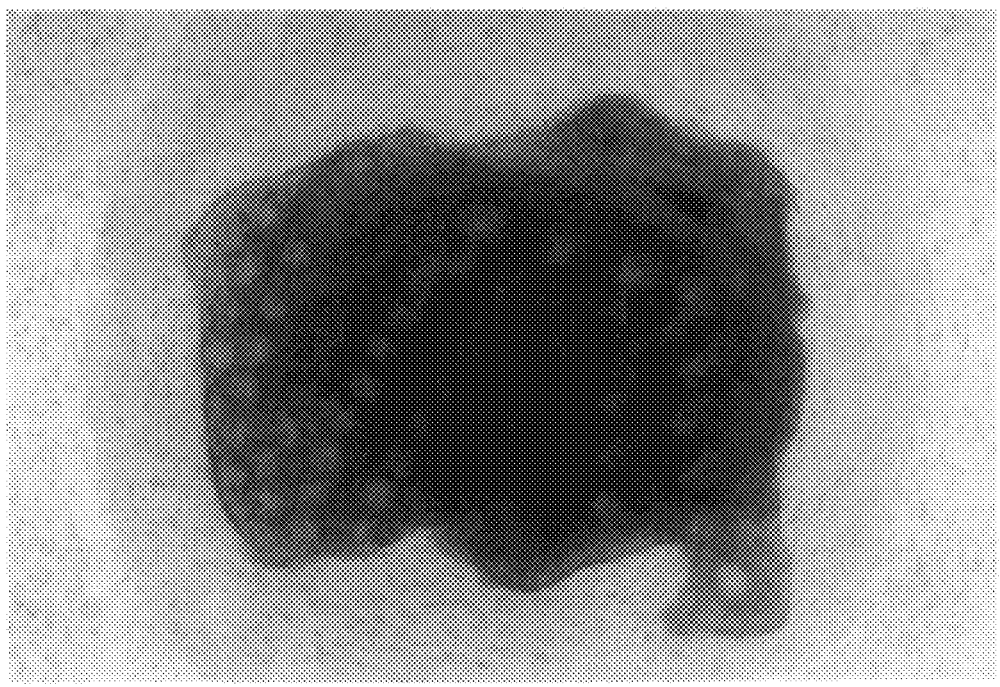
FIG. 5 is a photomicrograph of the histological shape of a mouse maxillary skin at the start of culture when its organ culture was performed in the presence of the epimorphin antagonist of the present invention.
Figure 6:
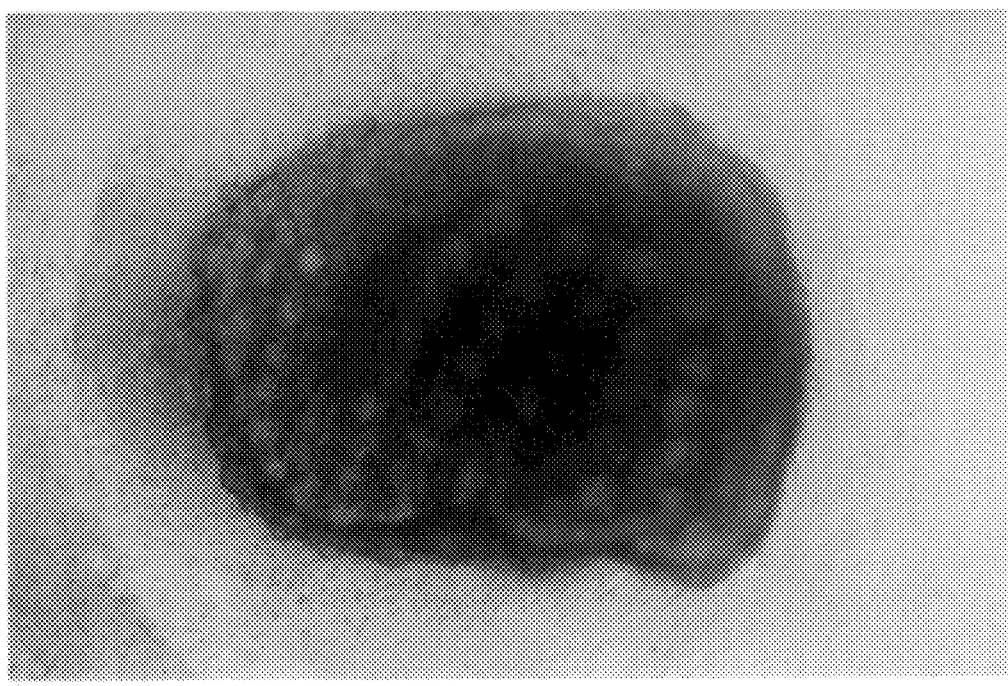
FIG. 6 is a photomicrograph of the histological shape after 3 days of culture when the organ culture of the mouse maxillary skin was performed in the presence of the epimorphin antagonist of the present invention.
Figure 7:
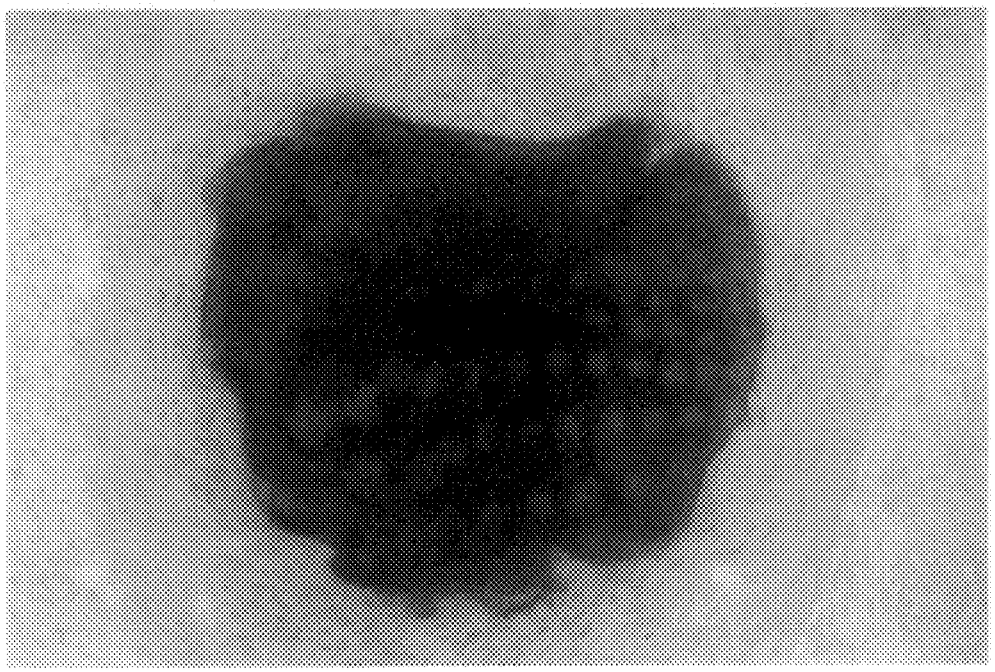
FIG. 7 is a photomicrograph of the histological shape of a mouse maxillary skin at the start of culture when its organ culture was performed in the absence of the epimorphin antagonist of the present invention.
Figure 8:
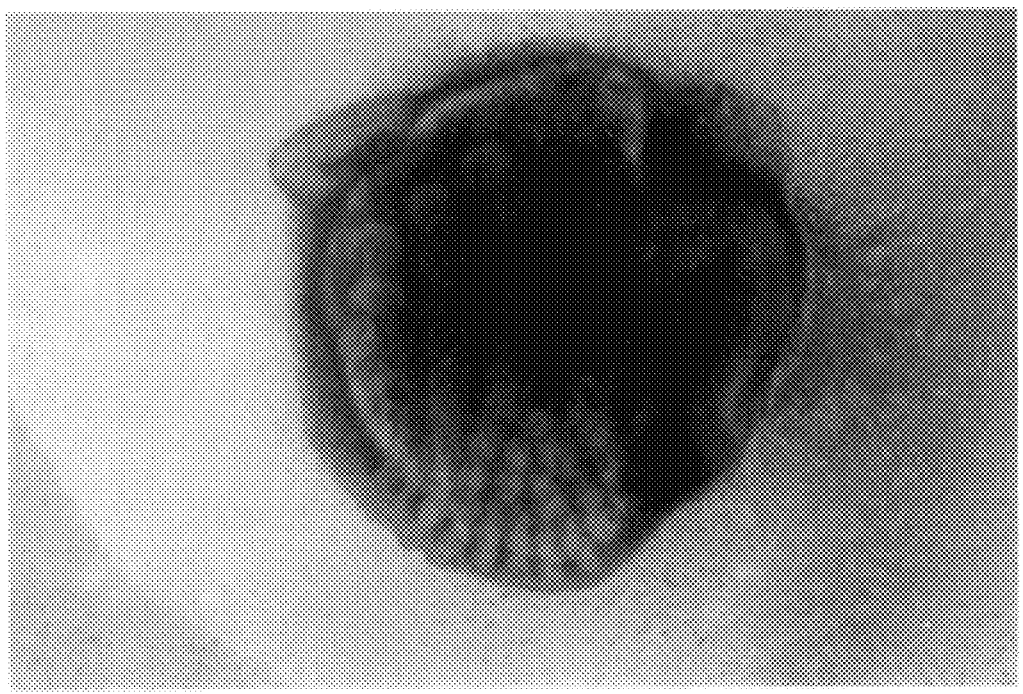
FIG. 8 is a photomicrograph of the histological shape after 3 days of culture when the organ culture of the mouse maxillary skin was performed in the absence of the epimorphin antagonist of the present invention.

A maxillary skin was removed from the fetus of the ICR pregnant mouse (Nippon Charles River, 13 days of gestation) under a stereoscopic microscope. The maxillary skin taken was placed on Nuclepore membrane filter (SN 110419) floated on a culture medium (DH medium, or 0.35 mg/ml polypeptide A-containing DH medium). Organ culture was performed in 5% $CO_2$ at 37° C. to investigate the effect of polypeptide A on the morphogenesis of the hair follicle. As shown in FIGS. 7 and 8, when organ culture used DH medium, the morphogenesis of normal hair follicles from the maxillary skin proceeded, and the formation of a plurality of hair follicles was confirmed. When the maxillary skin was organ cultured in the culture medium containing polypeptide A, on the other hand, the morphogenesis of hair follicles was markedly inhibited (FIGS. 5 and 6). This manner of inhibition of morphogenesis was exactly the same as in treatment with MC-1, i.e., antibodies inhibiting the function of epimorphin. Hence, it is clear that the polypeptide A of the present invention inhibits the hair follicle morphogenetic action of epimorphin on a maxillary skin.

Industrial Applicability

The epimorphin antagonist of the present invention has the activity of specifically inhibiting the morphogenic activity of epimorphins on epithelial tissue. Thus, it is useful as the active ingredient of a pharmaceutical for the treatment and/or prevention of diseases ascribed to the excessive expression of epimorphin, or as the active ingredient of a hair growth inhibitor.

---

What is claimed is:

1. An isolated polynucleotide encoding an epimorphin antagonist having epimorphin antagonist activity, wherein the epimorphin antagonist is a polypeptide consisting of amino acid sequence SEQ ID NO: 2 or SEQ ID NO: 3.

2. An isolated polynucleotide encoding an epimorphin antagonist having epimorphin antagonist activity, wherein the epimorphin antagonist is a polypeptide consisting of the amino acid sequence set forth in SEQ ID NO: 4 or the amino acid sequence of the 1st to the nth amino acid of SEQ ID NO: 4, wherein n denotes an integer of 20 to 83.

3. An isolated polynucleotide encoding an epimorphin antagonist having epimorphin antagonist activity, wherein the epimorphin antagonist is a polypeptide consisting of the amino acid sequence set forth in SEQ ID NO: 5 or the amino acid sequence of the 1st to the nth amino acid of SEQ ID NO: 5, wherein n denotes an integer of 20 to 83.

* * * * *